(12) United States Patent
Murata et al.

(10) Patent No.: US 11,141,190 B2
(45) Date of Patent: Oct. 12, 2021

(54) MEDICAL OVERTUBE DEVICE

(71) Applicant: OLYMPUS CORPORATION, Tokyo (JP)

(72) Inventors: Takeshi Murata, Tokyo (JP); Hiroyoshi Kobayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 52 days.

(21) Appl. No.: 16/700,139

(22) Filed: Dec. 2, 2019

(65) Prior Publication Data
US 2020/0100813 A1 Apr. 2, 2020

Related U.S. Application Data

(63) Continuation of application No. PCT/JP2017/020803, filed on Jun. 5, 2017.

(51) Int. Cl.
*A61B 17/34* (2006.01)
*A61B 34/00* (2016.01)
(Continued)

(52) U.S. Cl.
CPC .......... *A61B 17/3423* (2013.01); *A61B 34/71* (2016.02); *A61B 1/00154* (2013.01);
(Continued)

(58) Field of Classification Search
CPC ............ A61B 17/29; A61B 17/320016; A61B 17/3423; A61B 1/00149; A61B 1/00154;
(Continued)

(56) References Cited

U.S. PATENT DOCUMENTS 5,179,935 A * 1/1993 Miyagi ................ A61B 1/0055
600/108
6,960,162 B2 * 11/2005 Saadat ................ A61B 1/0008
600/114
(Continued)

FOREIGN PATENT DOCUMENTS

EP          3143922 A1      3/2017
JP       H07-159700 A       6/1995
(Continued)

OTHER PUBLICATIONS

International Search Report dated Aug. 22, 2017 issued in PCT/JP2017/020803.

*Primary Examiner* — Elizabeth Houston
*Assistant Examiner* — Alyssa M Keane
(74) *Attorney, Agent, or Firm* — Scully, Scott, Murphy & Presser, P.C.

(57) ABSTRACT

A medical overtube device has a main body formed by articulating a plurality of nested units into a first group of nested units and a second group of nested units and is bendable in a longitudinal direction thereof; a first shape-fixation mechanism configured to fix a shape of the first group which has a first wire, both end of the first wire coupled to the first group of nested units and a first pulley configured to be wound by the first wire; and a second shape-fixation mechanism configured to fix a shape of the second group which has a second wire, both end of the second wire coupled to the second group of nested units; and a second pulley configured to be wound by the second wire, wherein the first shape-fixation mechanism is configured to release the fixed shape of the first group independently from the second shape-fixation mechanism.

6 Claims, 13 Drawing Sheets

(51) Int. Cl.
*A61B 1/00* (2006.01)
*A61B 17/29* (2006.01)
*A61B 17/32* (2006.01)
*A61B 17/00* (2006.01)
*A61M 25/06* (2006.01)

(52) U.S. Cl.
CPC ....... *A61B 17/29* (2013.01); *A61B 17/320016* (2013.01); *A61B 34/74* (2016.02); *A61B 2017/00199* (2013.01); *A61B 2017/00323* (2013.01); *A61B 2017/00862* (2013.01); *A61B 2017/3452* (2013.01); *A61M 25/0662* (2013.01)

(58) Field of Classification Search
CPC ........ A61B 1/0055; A61B 2017/00199; A61B 2017/00314; A61B 2017/00323; A61B 2017/00862; A61B 2017/3452; A61B 2034/301; A61B 2090/508; A61B 34/30; A61B 34/37; A61B 34/71; A61B 34/74; A61B 1/0078; A61B 2034/715; A61B 2017/00318; A61B 2017/00327; A61B 2017/00331; A61B 1/00147; A61B 1/00131; A61B 1/00133; A61B 1/00135; A61B 1/005; A61B 1/0051; A61B 1/0057; A61B 1/008; A61B 1/01; A61B 1/00156; A61B 1/0133; A61B 1/0016; A61B 2017/003; A61B 2017/00305; A61B 2017/00309; A61B 2017/2908; A61B 1/0056; A61M 25/0662; A61M 25/0133; A61M 25/0138; A61M 25/0147; A61M 2025/015
USPC ........................................................ 600/144
See application file for complete search history.

(56) References Cited

U.S. PATENT DOCUMENTS

| | | | | |
|---|---|---|---|---|
| 2004/0138525 | A1* | 7/2004 | Saadat | A61B 1/313 600/104 |
| 2004/0138529 | A1* | 7/2004 | Wiltshire | A61B 1/0055 600/144 |
| 2006/0069304 | A1 | 3/2006 | Takemoto et al. | |
| 2009/0216083 | A1* | 8/2009 | Durant | A61B 1/0055 600/130 |
| 2016/0360949 | A1* | 12/2016 | Hyodo | A61B 1/04 |
| 2016/0374772 | A1* | 12/2016 | Hasegawa | A61B 34/37 606/130 |

FOREIGN PATENT DOCUMENTS

| | | |
|---|---|---|
| JP | 2003-093323 A | 4/2003 |
| JP | 2006-087687 A | 4/2006 |
| JP | 2007-511247 A | 5/2007 |
| JP | 2009-279412 A | 12/2009 |
| JP | 2014-124475 A | 7/2014 |
| JP | 2015-217017 A | 12/2015 |

* cited by examiner

MEDICAL OVERTUBE DEVICE

This application is a continuation application based on a PCT International Application No. PCT/JP2017/020803, filed on Jun. 5, 2017. The content of the PCT International Application is incorporated herein by reference.

TECHNICAL FIELD

The present invention relates to a medical overtube device.

BACKGROUND ART

Conventionally, a medical manipulator configured for an operator to operate an observation means and a treatment tool in a state in which the observation means and the treatment tool are inserted inside a body.

In a situation in which such medical manipulator is introduced into the body, the observation means and the treatment tool are inserted through a medical overtube device (hereinafter described as "overtube") and introduced into the body.

An overtube having a shape which can be fixed at an arbitrary timing is known. The overtube disclosed in Japanese Unexamined Patent Application, First Publication No. 2009-279412 and Japanese Unexamined Patent Application, First Publication No. 2014-124475 is configured by lining up a plurality of nested-structure elements along an axial direction, wherein each nested-structure element has a tubular shape. When the overtube is compressed in a longitudinal direction by a wire or suction, a distance between two of the plurality of nested-structure elements decreases. The distance between two of the plurality of nested-structure elements decreases such that it is difficult for the plurality of nested-structure elements to relatively move with each other and the shape of the overall overtube is fixed.

SUMMARY

According to a first aspect of the present invention, a medical overtube device has a main body formed by articulating a plurality of nested units into a first group of nested units and a second group of nested units, wherein the main body is configured to be bendable in a longitudinal direction thereof; a first shape-fixation mechanism configured to fix a shape of the first group of nested units, the first shape-fixation mechanism has a first wire, both ends of the first wire coupled to the first group of nested units; and a first pulley configured to be wound by the first wire; and a second shape-fixation mechanism configured to fix a shape of a second group of nested units, the second shape-fixation mechanism has a second wire, both ends of the second wire coupled to the second group of nested units; and a second pulley configured to be wound by the second wire, wherein the first shape-fixation mechanism is configured to release the fixed shape of the first group of nested units independently from the second shape-fixation mechanism.

According to a second aspect of the present invention, the medical overtube device according to the first aspect may further have a third pulley configured to be wound by a third wire, wherein one end of the third wire may be coupled to a first rotation shaft of the first pulley, and another end of the third wire may be coupled to a second rotation shaft of the second pulley.

According to a third aspect of the present invention, in the medical overtube device according to the first aspect, the first wire may be further configured to bend the first group of nested units actively.

According to a fourth aspect of the present invention, in the medical overtube device according to the first aspect, the second wire may have an elongated coil sheath configured to insert the first wire therein; and an engagement member coupled to a distal end of the elongated coil sheath, wherein the engagement member is configured to absorb force from a proximal end of the first group of nested units.

According to a fifth aspect of the present invention, the medical overtube device according to the first aspect may further have an advancement/retraction mechanism configured to advance and retract the first group of nested units with respect to the second group of nested units in the longitudinal direction of the main body.

DESCRIPTION OF EMBODIMENT

A first embodiment of the present invention will be described by referring to FIG. 1 to FIG. 11.

Figure 1:
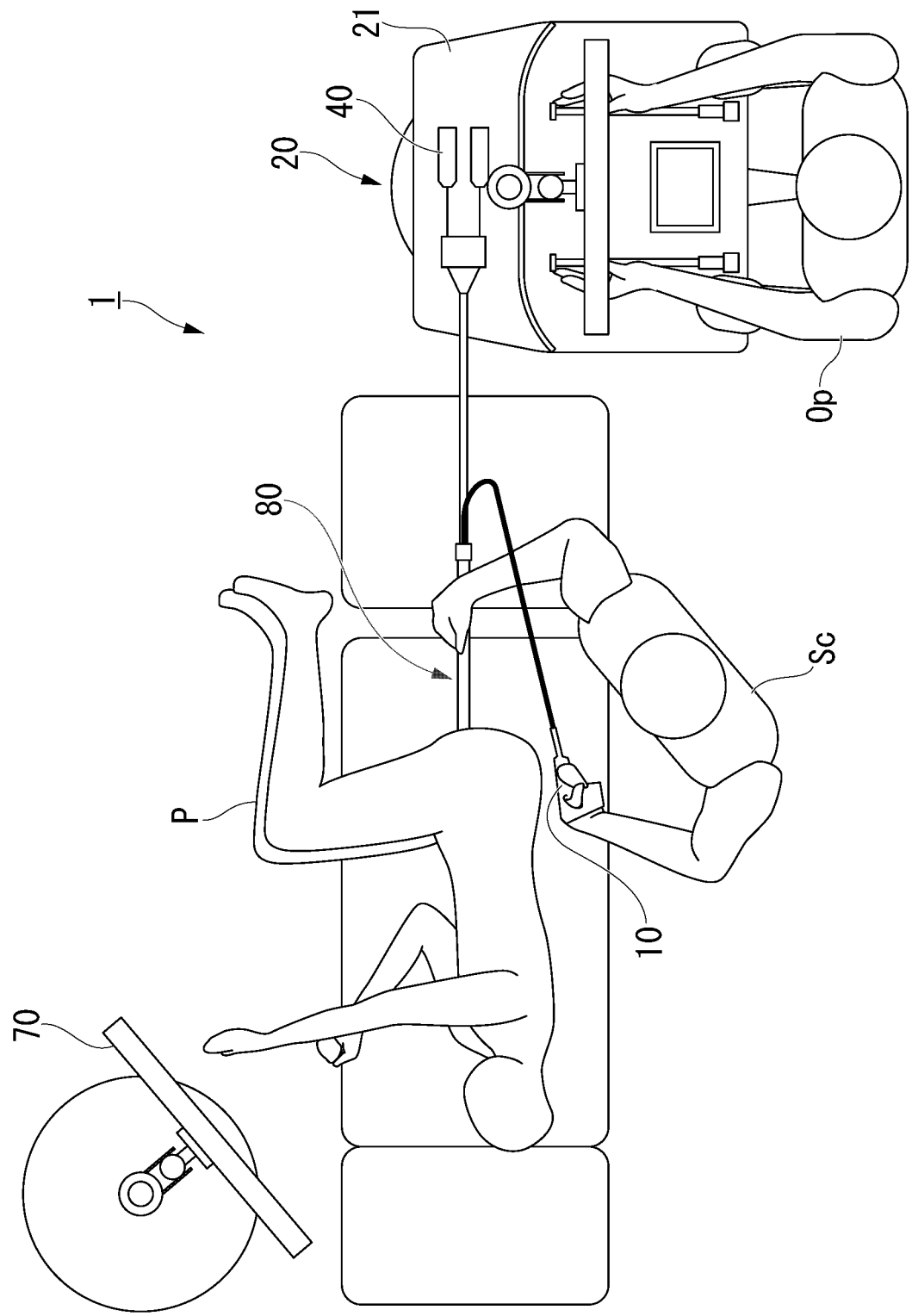
FIG. 1 is a schematic view showing a medical manipulator system having a medical overtube device according to a first embodiment of the present invention.

FIG. 1 is a view showing a medical manipulator system (hereinafter described as "system") 1 having an overtube device (hereinafter described as "overtube") according to the present embodiment. The system 1 has an endoscope 10 configured to observe the inside of the body of a patient P, a medical manipulator (hereinafter described as "manipulator") 20 configured for performing treatment inside the body of the patient P, and a flexible overtube 80 for inserting the endoscope 10 and the manipulator 20 through thereof. The overtube 80 is an embodiment of the overtube of the present invention.

The endoscope 10 can be adopted by suitably selecting from various conventional configurations in consideration of performance and usage.

The manipulator 20 has a console 21 operated by an operator Op and a treatment tool unit 40 attached to the console 40.

Figure 2:
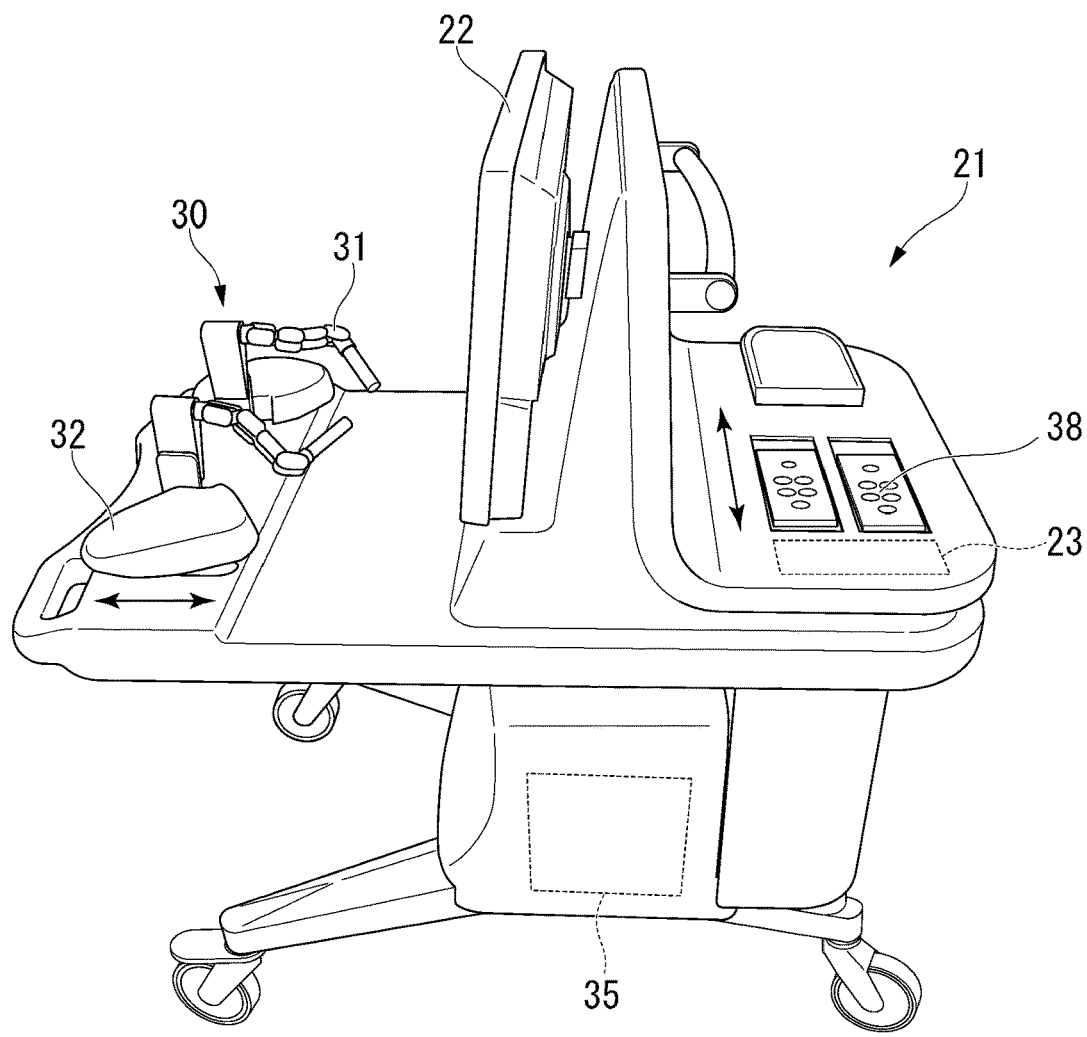
FIG. 2 is a view showing a console of the medical manipulator system.

FIG. 2 is a view showing the console 21. The console 21 has an operation portion 30 to which the operator Op inputs is configured to perform input operations, a control unit 35 configured to operate the treatment tool unit 40 according to the output from the operation portion 30, an attachment portion (advance/retraction driver) 30 to which the treatment tool unit 40 is attached, and a monitor 22.

The monitor 22 is coupled to the endoscope 10 and configured to display images acquired by the endoscope 10.

Figure 3:
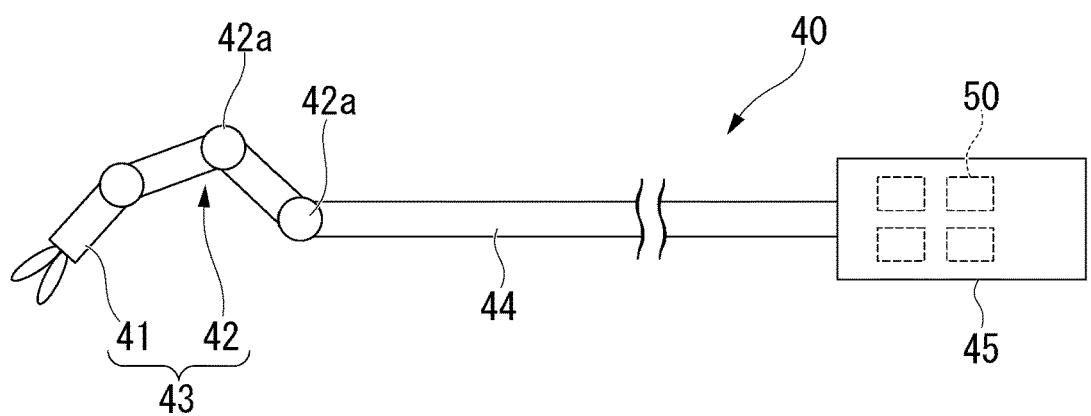
FIG. 3 is a schematic view showing a treatment tool unit in the medical manipulator system.

FIG. 3 is a schematic view showing the treatment tool unit 40. The treatment tool unit 40 has an arm portion 43 including a treatment tool (end effector) 41 and an arm 42 to which the treatment tool 41 is attached to, and a driving unit 45 configured to drive the treatment tool 41 and the arm 42. A region between the arm portion 43 and the driving unit 45 is a connection portion 44 having flexibility. In the driving unit 45, a plurality of driving sources 50 corresponding to a plurality of joints 42a disposed in the arm 42 are provided. A plurality of transmission members 47 are connected to the plurality of joints 42a respectively through the connection portion 44, wherein each of the plurality of transmission members 47 is configured to transfer a driving force from each driving source 50 to the corresponding joint 42a.

Examples of the driving source 50 and the transmission member 47 can be given as a motor and a wire respectively.

Figure 4:
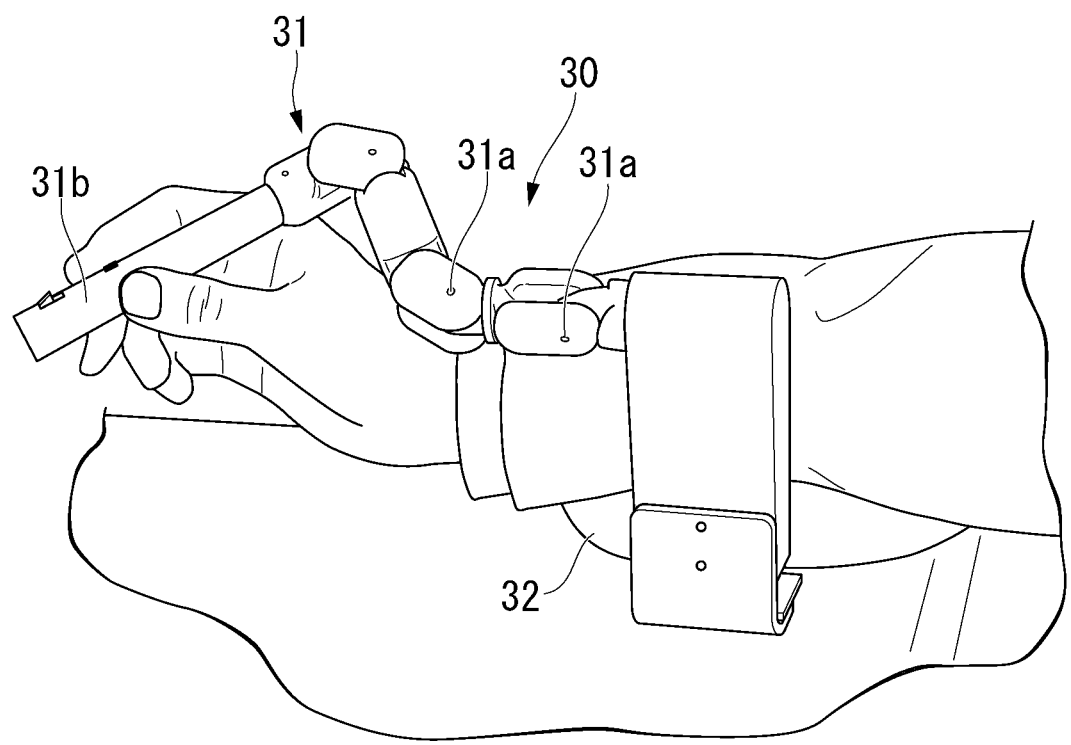
FIG. 4 is a view showing an operation portion in the console.

FIG. 4 is a view showing an operation portion 30 of the console 21. The operation portion 30 has an operation arm 31 configured to perform the operation input with respect to the arm 42 and a base to which the operation arm 31 is attached.

The operation arm 31 has a plurality of joints 31a. A number of the joints 31a is equal to a number of the joints 42a of the arm 42, and embodiments of rotation axes of each joint are the same. An encoder (not shown) and the like is provided in each joint 31a so as to be able to determine a rotation angle. When the operator Op operates the operation arm 31 to an arbitrary configuration or shape, the control unit 35 generates operation signals of the plurality of driving sources corresponding each joint 42a according to the determination values determined by the encoder provided in each joint 31a. The driving sources 50 are operated due to the operation signals such that each joint 42a of the arm 42 is driven and a shape of the arm portion 43 becomes similar to the shape of the operation arm 31.

A treatment operation portion 31b configured to operate the treatment tool 31 is provided at a distal end portion of the operation arm 31. A specific embodiment of the treatment operation portion 31b can be suitably set according to the configuration of the treatment tool 41. For example, in a situation in which the treatment tool 41 is a pair of grasping forceps, the treatment operation portion 31b may have an equivalent configuration with that of the pair of grasping forceps. In a situation in which the treatment tool 41 is a knife used by being supplied with electrical power, the treatment operation portion 31b may be a configuration having a switch bottom to switch ON/OFF of the electrical power.

The base 32 is attached to the console 21 to be relatively movable with respect to the console 21. When the base 32 is relatively moved with respect to the console 21, the attachment portion 38 relatively moves with respect to the console 21. Accordingly, the treatment tool unit 40 attached to the attachment portion 38 can be relatively moved with respect to the console 21.

Figure 5:
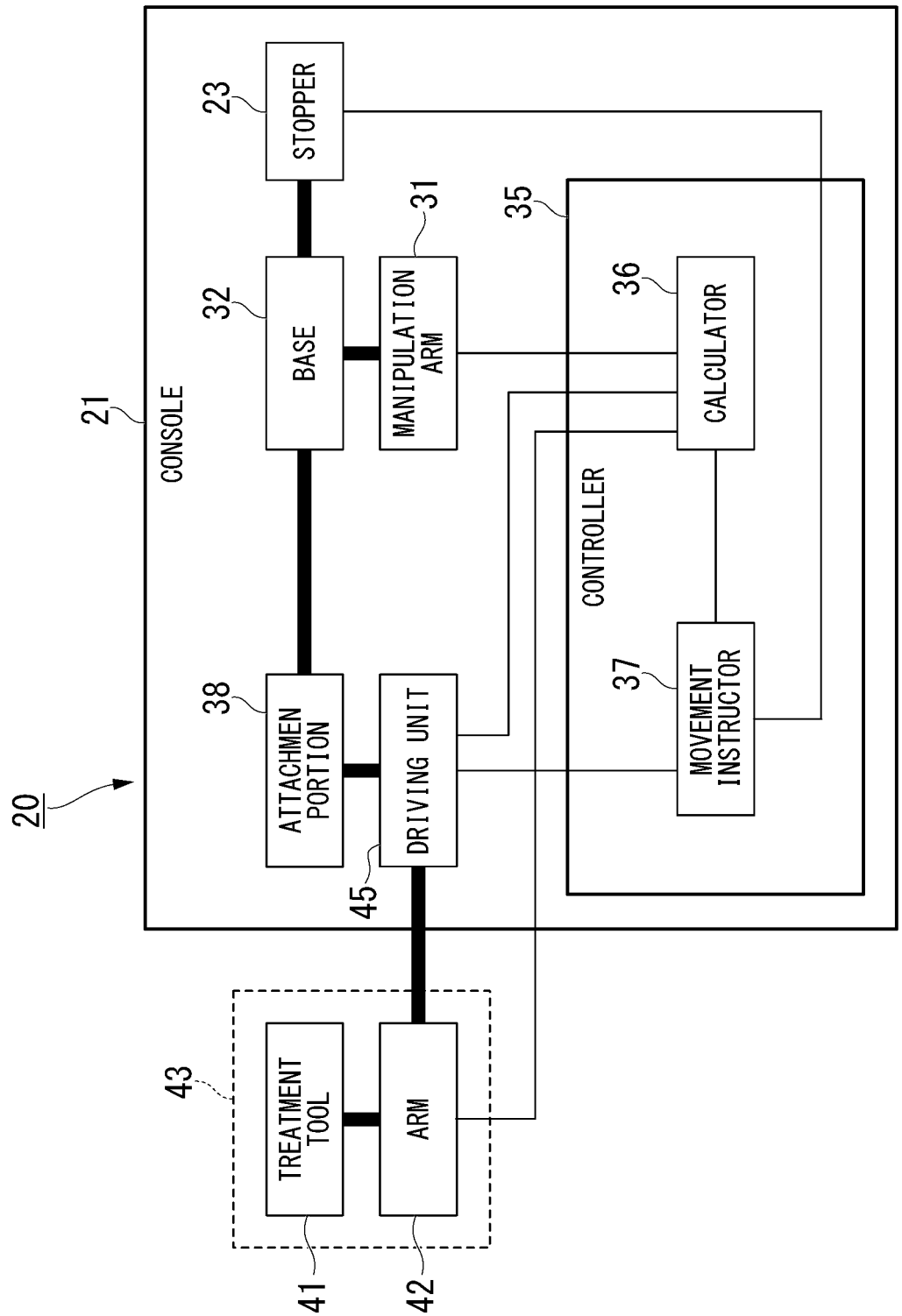
FIG. 5 is a function block diagram of a medical manipulator in the medical manipulator system.
Figure 6:
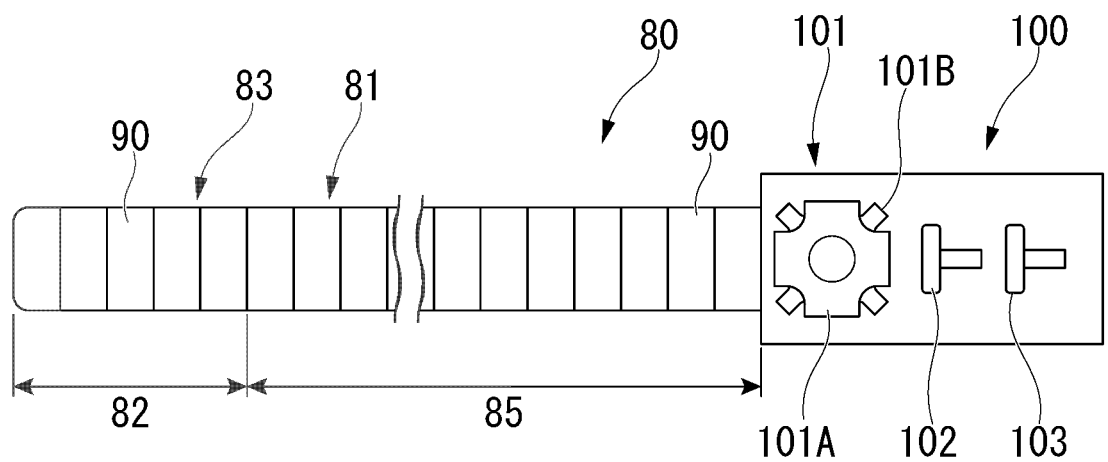
FIG. 6 is an overall schematic view showing the medical overtube device.

FIG. 5 is a functional block diagram of the manipulator 20 in a state in which the treatment tool unit 40 is attached to the console 21. In FIG. 6, the monitor 22 is omitted. In FIG. 6, the bold lines connecting the configurations indicate physical couplings capable of transmitting motive power, and fine lines connecting the configurations indicate logical couplings capable of performing signal transmission.

In the manipulator 20 according to the present embodiment, for example, the base 32 and the attachment portion 38 are physically coupled by a belt, a chain, and the like. Accordingly, when the base 32 is relatively moved with respect to the console 21, the attachment portion 38 relatively moves with respect to the console 21 according to the movement of the base 32. At this time, the operation arm 31 moves together with the base 32, and the driving unit 45 attached to the attachment portion 38 moves together with the attachment portion 38.

As described above, the driving unit 45 is physically coupled with the arm portion 43 by the transmission member 47. If necessary, the treatment tool 41 is connected to the driving source 50 by the transmission member.

The control unit 35 has a calculation unit 36 configured to perform various calculations and determinations, and an operation instruction unit 37 logically coupled with the calculation unit 36, wherein the operation instruction unit 37 is configured to operate each part of the manipulator 20 in accordance with the output of the calculation unit 36.

The calculation unit 36 is logically coupled to the operation arm 31, the arm 42, and the driving unit 45. The operation instruction unit 37 is logically coupled to the driving unit 45, and the operation instruction unit 37 is configured to be able to operate each driving source 50 of the driving unit 45 by transmitting the operation signals thereto.

The hardware configuration of the control unit 35 can be made by a combination of a processor, a logic circuit, a memory, and a circuit connecting such configurations. The hardware configuration may include two or more than two elements described above and either of the processor or the logic circuit may not be included. As another embodiment, the control unit 35 may be configured to have two or more than two individual housings, and the housings may be connected by a network (including wireless communication).

Next, a structure of the overtube 80 will be described. FIG. 6 is a schematic view showing the overall overtube 80. The overtube 80 has a tubular main body 81 and an operation portion 100 provided at a proximal end portion of the main body 81.

The main body 81 is configured by articulating a plurality of nested-structure elements (hereinafter described as "element" or "nested unit") 90 formed in tubular shapes along an axial direction (longitudinal direction of the main body 81). The main body 81 is configured to be bendable due to a change of a positional relationship between the adjacent elements 90.

As shown in FIG. 6, the main body 81 has a first region (first group of nested units) 82 at the distal end side, and a second region (second group of nested units) 85 at the proximal end side with respect to the first region 82. The first region 82 has an active-bending portion 83 which can be bent to a direction desired by the operator. The active-bending portion 83 may be a part of the first region 82 or the whole first region 82.

Figure 7:
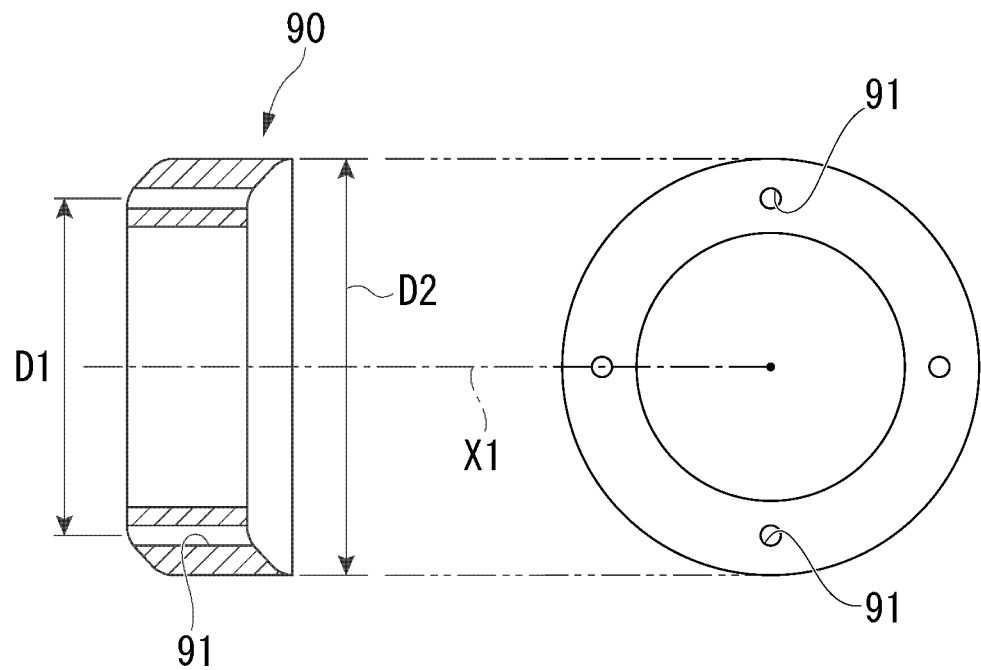
FIG. 7 is a view showing a nested-structure element configuring the overtube device.

FIG. 7 is a view showing a basic shape of the element 90. A sectional view of the element 90 along the axis X1 is shown at the left side of FIG. 7, and the right side of FIG. 7 is a front view of the element 90. The element 90 formed in a tubular shape has a distal-end-side diameter D1 which is smaller than a proximal-end-side diameter D2. Accordingly, the distance between the adjacent elements 90 can be changed by making the distal end portion of the element 90 disposed relatively proximally to enter the proximal end portion of the element 90 disposed relatively distally.

As shown in FIG. 7, the element 90 disposed in the first region 82 has four wire lumens 91. Each wire lumen 91 is formed to be substantially parallel to the axis X1, and two adjacent wire lumens 91 are apart from each other by a rotation angle of 90 degrees in a circumferential direction thereof.

The element 90 in the second region 85 is disposed in a position such that the wire lumen 91 shifts by a rotation angle of 45 degrees in the circumferential direction with respect to the wire lumen 91 of the element 90 in the first region 82.

Figure 8:
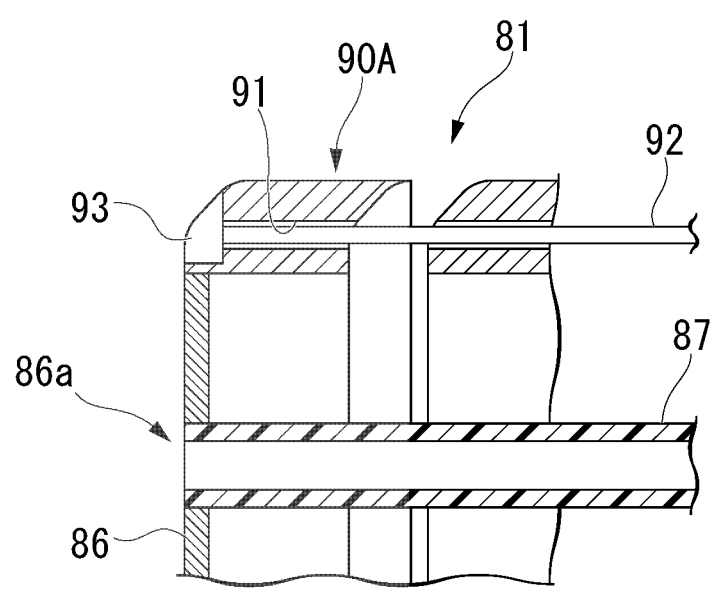
FIG. 8 is a partial sectional view of the overtube device.

A part of a sectional view of the distal end portion of the main body 81 along the axis X1 is shown in FIG. 8. A plate 86 in which a plurality of openings 86a (only one is shown in FIG. 8) are formed is attached to the element 90A disposed at the most distal end side, wherein the endoscope 10 and the treatment tool 41 protrude from the plurality of openings 86a. A plurality of tubes 87 (only one is shown in FIG. 8) function as channels for inserting through the endoscope 10 and the treatment tool 41 are connected to the plurality of openings 86a respectively. Each tube 87 extends to the operation portion 100 through the inside space of the main body 81.

An angle wire 92 for driving the active-bending portion 83 is inserted through each wire lumen 91 in the first region 82. An end portion of each angle wire 92 is attached to an engagement member 93 by caulking. Each engagement member 93 is fixed to the element 90A. By attaching the engagement member 93 to the element 90A, it is possible to prevent each angle wire 92 from being withdrawn from the element 90A when the active-bending portion 83 is driven. In the second region 85, each angle wire 92 extends to the operation portion 100 through the inside space of the main body 81 rather than passing through the wire lumen 91.

As shown in FIG. 6, the operation portion 100 has an angle knob 101 for operating the active-bending portion 83, a first slider (first shape-fixation mechanism) 102 for switching ON/OFF of fixing the shape of the first region 82, and a second slider (second shape-fixation mechanism) 103 for switching ON/OFF of fixing the shape of the second region 85.

Figure 9:
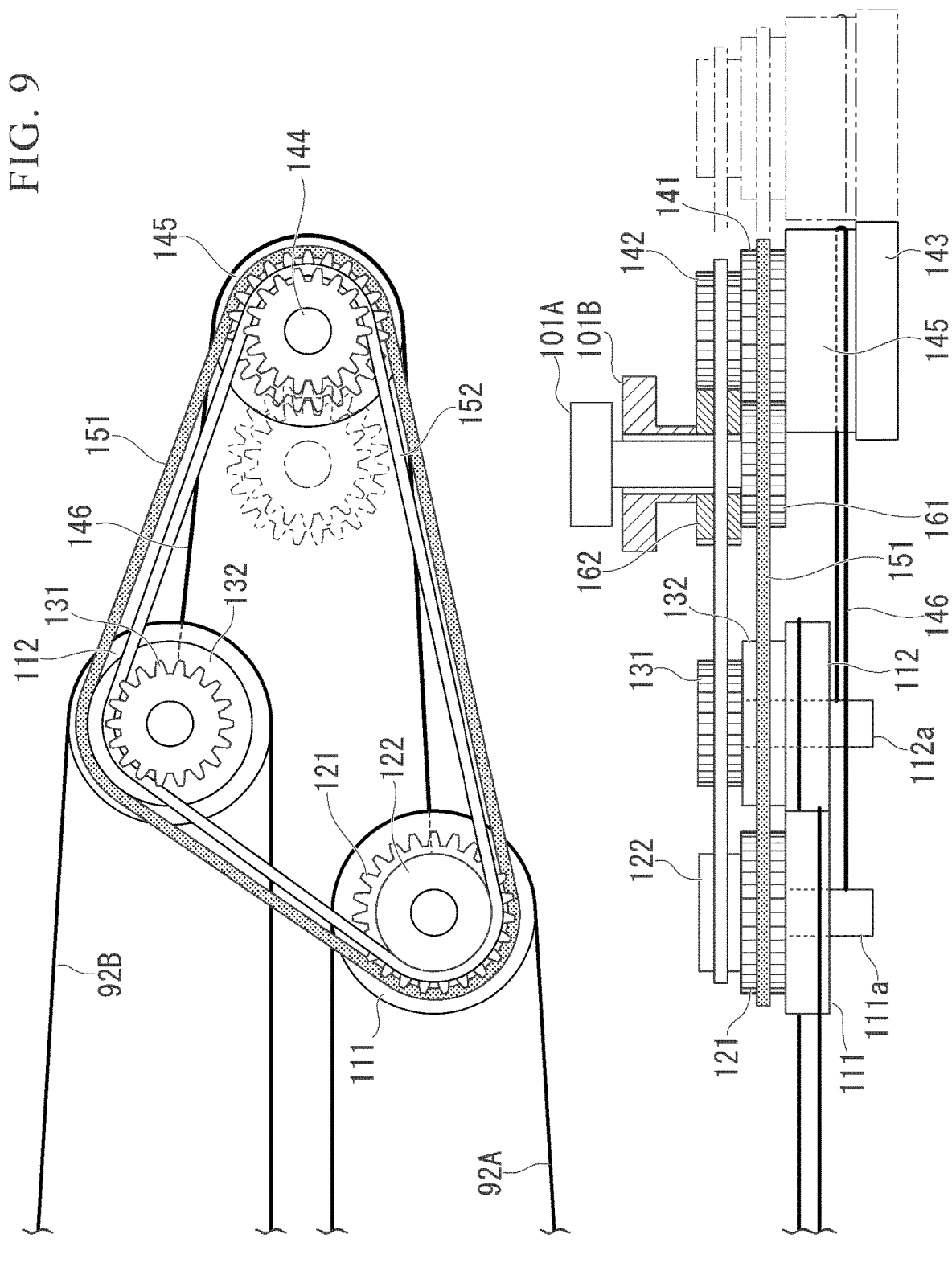
FIG. 9 is a schematic view showing a connection of an angle wire and the operation portion.

A connection between the angle wire 92 and the operation portion 100 is schematically shown in FIG. 9. In the present embodiment, an example of the configuration of the overtube 80 will be described to have two angle wires 92 (angle wire 92A and angle wire 92B). However, the configuration of the overtube 80 is not limited thereto. An intermediate portion of the angle wire 92A used for the driving in the left/right direction is wound on a first pulley 111 disposed in the operation portion 100. Two end portions of the angle wire 92A are fixed to the element 90A by the engagement member 93. Similarly, an intermediate portion of the angle wire 92B used for the driving in the up/down direction is wound on a second pulley 112 disposed in the operation portion 100, and two end portions of the angle wire 92B are fixed to the element 90A by the engagement member 93. The intermediate portion of the angle wire 92B is displaced by 90 degrees around the axis X1 in the second region 85. Accordingly, a rotation shaft 111a of the first pulley 111 and a rotation shaft 112a of the second pulley 112 are parallel with each other in the operation portion 100.

A first gear 121 is attached to the rotation shaft 111a to be coaxial with the first pulley 111. On the first gear 121, a spacer 122 having a torus shape is attached thereto. A second gear 131 is attached to the rotation shaft 112a to be coaxial with the second pulley 112. A spacer 132 having a torus shape is attached thereto between the second gear 131 and the second pulley 112. The space 122 and the spacer 132 are not fixed to the rotation shafts, and not linked with the rotation shafts.

In the operation portion 100, a rotation shaft 144 fixed to the plate 143 passes through a traction pulley 145 configured to pull the first pulley 111 and the second pulley 112, a first driving gear 141 configured to drive the first pulley 111, and a second driving gear 142 configured to drive the second pulley 112 such that the traction pulley 145, the first driving gear 141 and the second driving gear 142 are disposed to be coaxial. A first belt 151 is wound on the first driving gear 141, the first gear 121, and the spacer 132. A second belt 152 is wound on the second driving gear 142, the second gear 131, and the spacer 122.

As shown in FIG. 6, the angle knob 101 has a first knob 101A configured for the bending operation in the left/right direction and a second knob 101B configured for the bending operation in the up/down direction. As shown in FIG. 9, an operation gear 161 connected to the first knob 101A is engaged with the first driving gear 141. An operation gear 162 connected to the second knob 101B is engaged with the second driving gear 142.

In the state in which the angle knob 101 is engaged with the first driving gear 141 and the second driving gear 142, the tension is applied to the angle wire 92A, 92B so as to prevent the angle wire 92A, 92B from being loose. Accordingly, the operator can bend the active-bending portion 83 to a desired direction by suitably operating the angle knob 101.

The first slider 102 is connected to the plate 143 by a connection member (not shown). A traction member 146 formed by a wire and the like is wound on the circumference of the traction pulley 145. Two ends of the traction member 146 are connected to the rotation shaft 111a of the first pulley 111 and the rotation shaft 112a of the second pulley 112 respectively. According to the above-described configuration, the first region 82 and the first slider 102 are connected via the angle wire 92.

When the first slider 102 is slided toward the proximal end side of the operation portion 100, the plate 143 moves toward the proximal end side inside the operation portion 100. Accordingly, the rotation shaft 144 is apart from the angle knob 101 such that the engagement between the angle knob 101 and the first driving gear 141, the second driving gear 142 is dissolved. Furthermore, the first pulley 111 and the second pulley 112 connected to the traction pulley 145 via the traction member 146 move along the direction apart from the distal end of the main body 81 and the angle wires 92A, 92B are pulled.

The traction member 146 may be configured in another embodiment such as a member having a portion with different flexibility and rigidity (for example, a rod-shaped rigid body having a small diameter) besides the above-described embodiment of forming the traction member 146 by the angle wire only.

Figure 10:
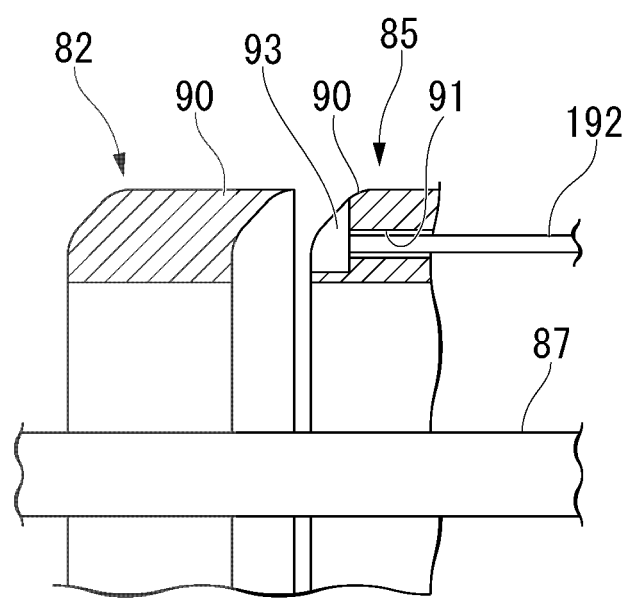
FIG. 10 is a partial sectional view showing a second region of the overtube device.

As shown in FIG. 10, a lock wire (second lock wire) 192 configured to fix the shape of the second region 85 passes through the wire lumen 91 of the element 90 disposed in the second region 85. Similar to the angle wire 92, two end portions of the lock wire 192 are attached to the engagement member 93, and each engagement member 93 is fixed to the element 90 disposed in the most distal end side in second region 85.

Figure 11:
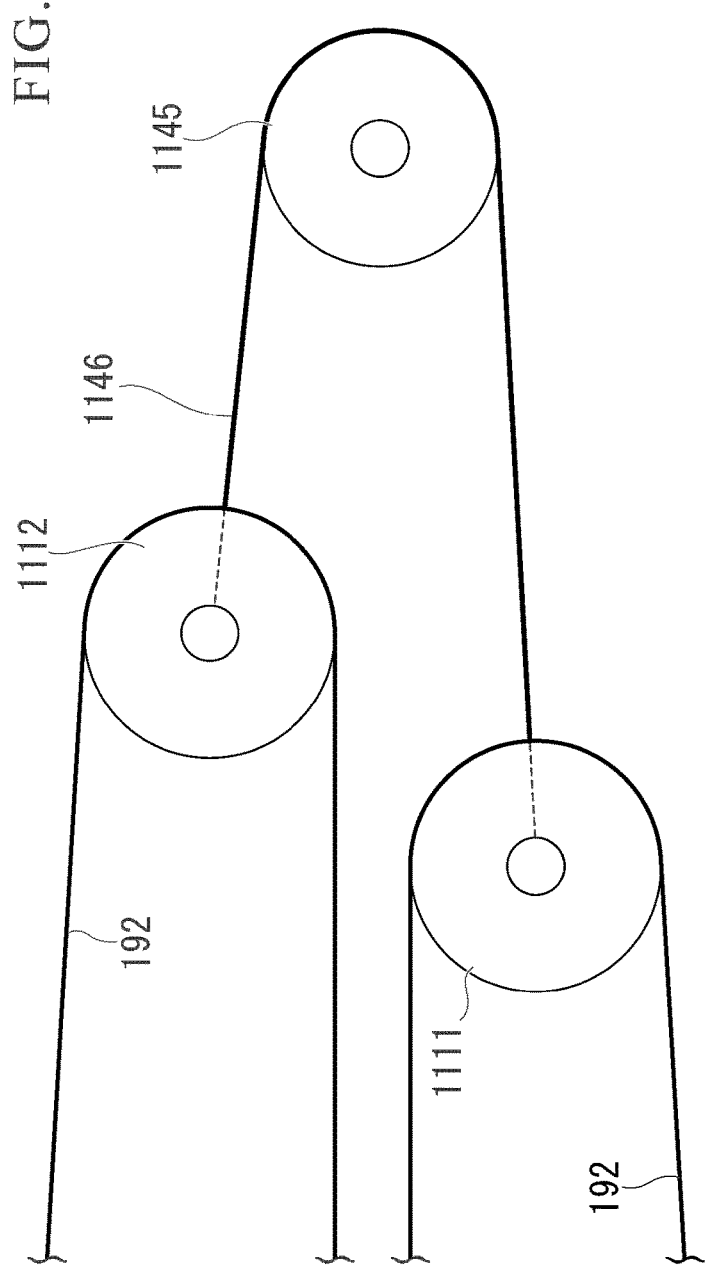
FIG. 11 is a schematic view showing a connection of a lock wire and the operation portion.
Figure 11:
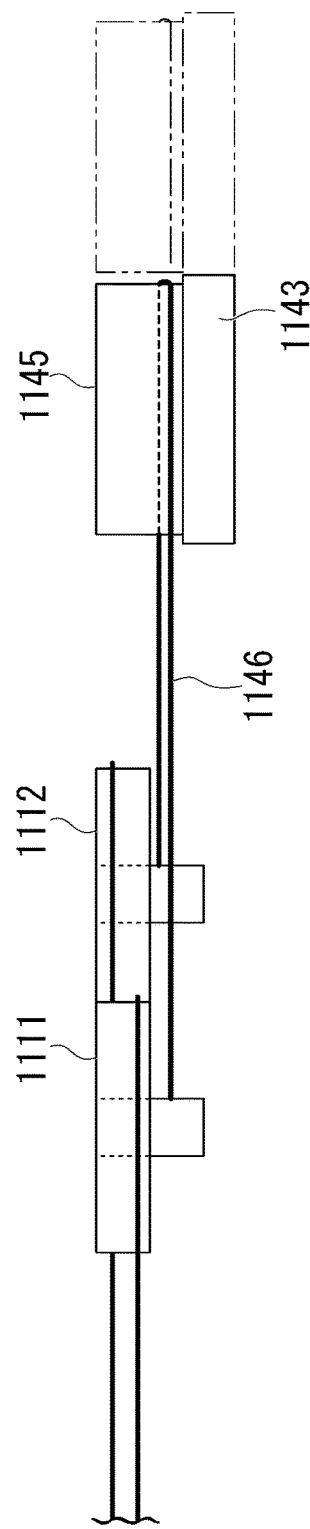

The connection between the lock wire 192 and the operation portion 100 are schematically shown in FIG. 11.

The embodiment of the connection between the lock wire 192 and the operation portion 100 is partially similar with that of the connection between the angle wire 92 and the operation portion 100. In other words, the second region 85 and the second slider 103 are connected to each other via the lock wire 192.

When the second slider 103 connected to the plate 1143 is slid toward the proximal end side of the operation portion 100, the first pulley 1111 and the second pulley 1112 connected to the traction pulley 1145 via the traction member 1146 move along the direction apart from the distal end of the main body 81. The intermediate portions of the two lock wires 192 are wound on the first pulley 1111 and the second pulley 1112 such that each lock wire 192 can be pulled toward the proximal end side of the operation portion 100 by operating the second slider 103. Both of the connection mechanism of the angle wire 92 and the operation portion 100, and the connection mechanism of the lock wire 192 and the operation portion 100 described above are disposed in the operation portion 100 without interfering each other.

The traction member 1146 may be configured in another embodiment such as a member having a portion with different flexibility and rigidity (for example, a rod-shaped rigid body having a small diameter) besides the above-described embodiment of forming the traction member 1146 by the angle wire only.

An operation of using the system 1 having the above-described configuration will be described according to an example of performing treatment to the colon. As shown in FIG. 1, the system 1 is operated by at least two persons including the operator Op operating the console 21 and a scopist (manipulator) Sc operating the overtube 80 and the endoscope 10.

Firstly, the scopist Sc inserts the endoscope 10 into the tube 87 for endoscope formed in the overtube 80. Subsequently the scopist Sc inserts the overtube through which the endoscope 10 is inserted into the anus of the patient P.

Next, the scopist Sc advances the overtube 80 in the colon while observing the images acquired by the endoscope 10 on the second monitor 70 (see FIG. 1), and introduces the distal end portion of the overtube 80 through which the endoscope 10 is inserted to the vicinity of the target site. The scopist Sc operates the angle knob 101 as necessary to bend the active-bending portion 83 to the desired direction. The scopist Sc slightly adjusts the endoscope 10 and the overtube 80 while receiving the instructions from the operator Op to determine a visual field for capturing the target site and then holds the endoscope 10 and the overtube 80.

According to the above-described operations, the overtube 80 is bent following the shape of the colon from the anus to the target site. When the scopist operates the first slider 102 and the second slider 103, the angle wire 92 and the lock wire 192 are pulled toward the operation portion 100. Thus, the distance between the elements 90 in the first region 82 and the second region 85 is decreased such that the distal end portion of the element 90 enters the proximal end side of the adjacent element. As a result, the friction force generated between the elements 90 increases so as to fix the shape of the main body 81.

Subsequently, the treatment tool unit 40 is inserted into the tube 87 for treatment tool from the arm portion 43 side. The arm portion 43 and the connection portion 44 of the treatment tool unit 40 apply a force to change the shape of the main body due to the elasticity; however, since the friction force between the elements 90 withstands this force so as to keep the shape of the main body 81, the treatment tool unit 40 advances in the main body 81 following the fixed shape of the main body 81. The treatment tool unit 40 is advanced until the treatment tool 41 is near the opening 86a of the plate 86. At this time, the operation arm 31 of the console 21 is kept in a substantially straight-line shape similar to the arm portion 43.

Next, the driving unit 45 of the treatment tool unit 40 is set to the attachment portion 38. When the driving unit 45 is set to the attachment portion 38, the driving unit 45 and the control unit 35 are logically coupled.

After the above-described operations are finished, the system 1 is in the state in which the manipulator 20 can be operated. The operator Op operates the console 21 while observing the images by the endoscope 10 so as to operate the treatment tool unit 40 to perform desired treatment with respect to the target site.

For example, in the situation of performing the procedures of Endoscopic Submucosal Dissection (ESD), since the target site covers a wide range, it is possible that the desired position cannot be accessed even if the treatment tool 41 is protruded at the maximum from the overtube 80 whose shape is fixed. In this case, the scopist Sc operates the first slider 102 to dissolve the traction by the angle wire 92. Thus, the shape fixation of the first region 82 only in the main body 81 is dissolved and the operation of the active-bending portion 83 by the angle knob 101 becomes available. The scopist Sc can operate the active-bending portion 83 to slightly adjust the position of the distal end portion of the main body 81 so as to assist the access by the operator Op.

According to the overtube 80 according to the present embodiment, as described above, the shape of the first region 82 is fixed by operating the first slider 102 and the shape of the second region 85 is fixed by operating the second slider 103. Accordingly, only the shape fixation of the first region 82 can be dissolved without dissolving the shape fixation of the second region 85. As a result, even if the main body 81 disposed in the body is long, the case in which the main body 81 goes away from the target site will not occur such that it is easy to adjust the position of the distal end portion of the main body 81.

By applying the overtube 80 to the system. 1, the usability of the system 1 can be significantly improved.

In the first region 82, the shape of the first region 82 is fixed by pulling the whole angle wire 92 using the traction pulley 145. In other words, the angle wire 92 configured to drive the active-bending portion 83 also has the function as the lock wire to fix the shape of the first region 82. Accordingly, it is not necessary to provide another lock wire besides the angle wire 92 such that it is easy to reduce the diameters of the element 90 and the main body 81.

Furthermore, the first pulley and the second pulley on which the angle wire 92 and the lock wire 192 are wound respectively are connected to the traction pulley 145 configured to pull the angle wire 92 and the lock wire 192 by the traction member 146 wounding on the traction pulley 145. Accordingly, the traction pulley 145 suitably rotates in accordance with the shapes of the first region 82 and the second region 85 before the shape fixation. As a result, regardless the shapes of the first region and the second region before the shape fixation, the plurality of angle wires and lock wires can be always equally pulled to suitably fix the shapes thereof.

According to the present embodiment, a lock wire may be provided in the first region besides the angle wire. In this case, the number of the wires attached to the overtube increases such that it is unfavorable for reducing the diameter thereof; however, it is easy to adjust the position of the distal end after inserting the overtube into the body while realizing the shape fixation function.

The first slider 102 and the second slider 103 may be connected to the rotation shaft of the pulley on which the angle wire 92 and the lock wire 193 are wound without using the traction pulley 145 and the traction member 146. In this case, it is easy to adjust the position of the distal end after inserting the overtube into the body while realizing the shape fixation function.

A second embodiment of the present invention will be described by referring to FIG. 12. An overtube according to the present embodiment is different from the overtube according to the first embodiment in the configuration of the second region. In the description below, the described common configurations will be assigned with the same reference sings and the description will be omitted.

Figure 12:
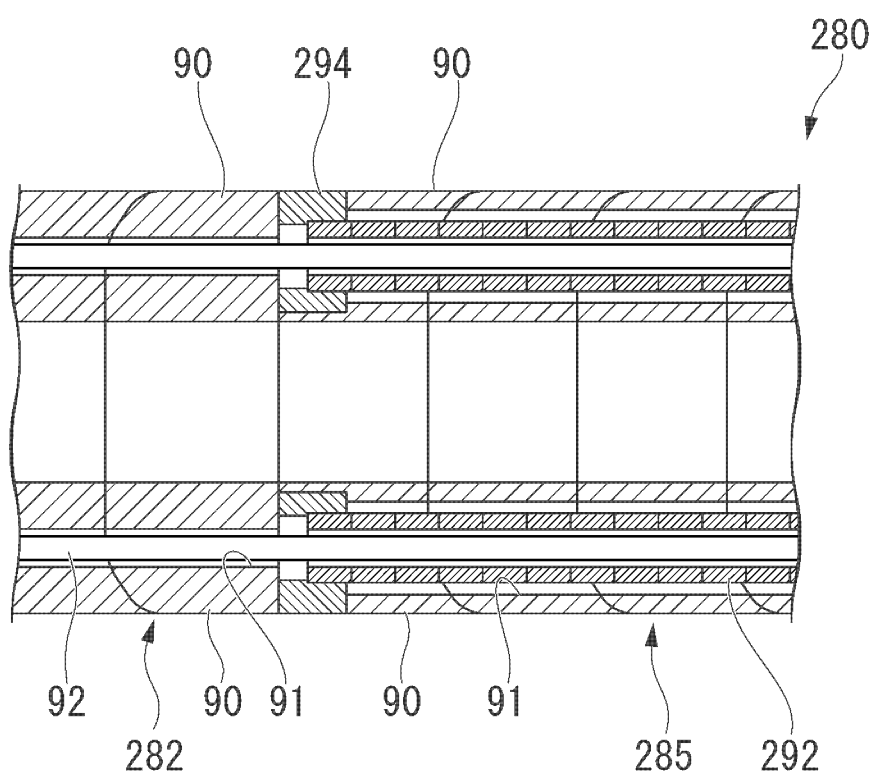
FIG. 12 is a schematic sectional view showing a medical overtube device according to a second embodiment of the present invention.

FIG. 12 is a partial sectional view showing a boundary portion between the first region 282 and the second region 285 in the overtube 280 according to the present embodiment. According to the present embodiment, the element 90 of the first region 280 and the element 90 of the second region 285 are disposed to have the same phase with the wire lumen 91.

The lock wire 292 configured for fixing the shape of the second region 285 is formed from a coil sheath having a tubular shape, wherein the coil sheath is made by winding metal strand wires. In the second region 285, the angle wire 92 extends to the operation portion 100 (not shown) through the inside of the lock wire 292 disposed in the wire lumen 91 of the element 90.

The engagement member 294 attached to the distal end portion of the lock wire 292 protrudes more distally than the element 90 which is the most distal configuration in the second region 285, and the engagement member 294 comes in contact with the proximal end side surface of the element 90 disposed in the most proximal end side in the first region 282.

Also, a pipe made from SUS (stainless steel), a multi-strip coil being strong against tension, and the like may be adopted as the lock wire 292.

In FIG. 12, the wire lumen 91 of the element 90 disposed in the second region 285 has a larger diameter than the wire lumen 91 of the element 90 disposed in the first region 282; however, such a dimension relationship is not absolutely necessary. For example, if the outer diameter of the lock wire 292 is determined such that the lock wire 292 can enter the wire lumen 91 of the element 90 disposed in the first region 282, the inner diameter of the wire lumen of the element 90 disposed in the first region 282 may be same with the inner diameter of the wire lumen of the element 90 disposed in the second region 285.

The operation when the overtube 280 having the above-described configuration according to the present embodiment will be described. When the first slider 102 configured for fixing the shape of the first region 282 is operated, similar to the first embodiment, the angle wire 92 is pulled toward the operation portion 100. Accordingly, the distance between the elements 90 in the first region decreases and the whole first region 282 approaches the operation portion 100.

At this time, the element 90 in the most proximal end side in the first region 282 presses the distal end portion of the lock wire 292 to which the engagement member 294 is attached rather than the element 90 of the second region 285. Accordingly, the press force due to the retraction of the first region 282 is not directly transmitted to the element 90 in the second region 285.

Furthermore, the engagement member 294 is fixed to the lock wire 292 configured from the coil sheath such that the press force received by the engagement member 294 is reduced or almostly eliminated due to the compression resistance of the lock wire 292. Accordingly, the press force due to the retraction of the first region 282 is almost not transmitted to the element 90 in the second region 285 via the engagement member 294.

Due to such effects, the shape of the second region 285 is almost not fixed while the operation of fixing the shape of the first region 280 in the overtube 280. As a result, added to the state in which only the shape of the second region is fixed, it is also possible to create a state in which only the shape of the first region is fixed.

According to the overtube 280 according to the present embodiment, similar to the first embodiment, it is easy to adjust the position of the distal end after inserting the overtube into the body while realizing the shape fixation function.

Furthermore, as described above, it is possible to create the state in which the shape of the second region is not fixed while fixing the shape of the first region 282 such that the usability of the overtube and the system configured by applying this configuration can be improved. The state in which only the shape of the first region is fixed is activated in the following situations. For example, in a situation of performing treatment with respect to the target site exist in the descending colon, it is possible to fix the shape of the first region 282 disposed inside the body to perform the treatment procedures while dissolving the shape fixation of the second region 285 whose most part is disposed outside the body to perform adjustment operations such as moving the operation portion 100 and the endoscope 10 to a position not to interfere with the lower limbs of the patient. As a result, the operations of the scopist Sc and the operator Op become easy.

Several embodiments and modification examples of the present invention have been described above, however, technical scope of the present invention is not limited to the embodiment and the application examples. Additions, omissions, substitutions and other changes in the structure are possible without departing from the spirit of the present invention.

For example, the overtube according to the present invention may be configured to fix the shape of the second region while performing various slight adjustment further in the first region. Hereinafter, such modification examples will be shown.

Figure 13:
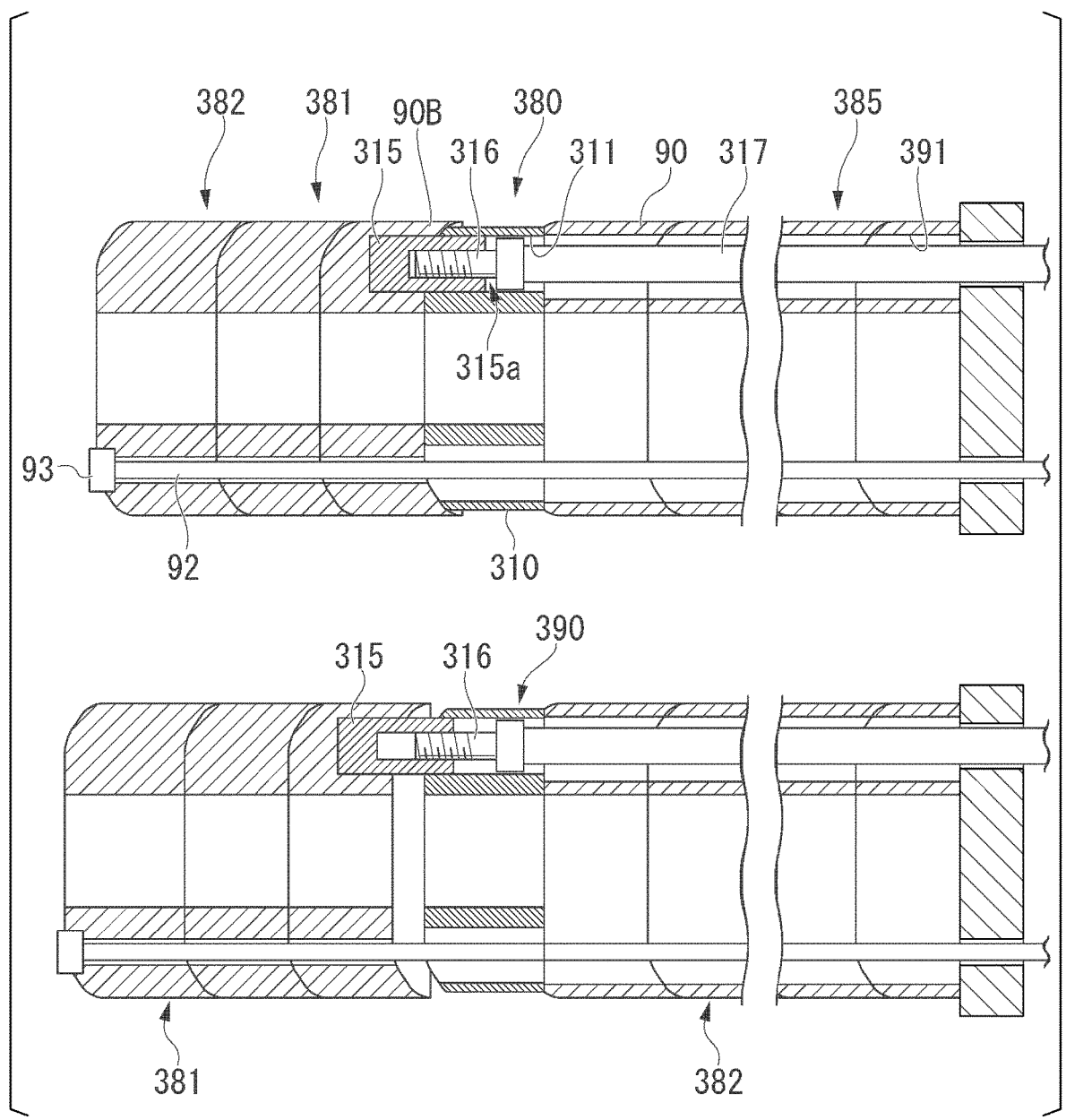
FIG. 13 is a schematic sectional view showing a medical overtube device according to a modification example of the present invention.

An overtube 380 shown in the schematic sectional view in FIG. 13 is a configuration example of fixing the shape of the second region 385 while the distal end of the first region 382 can advance or retract.

In FIG. 13, the lock wire configured to fix the shape of the second region 385 is disposed in a different phase in the circumferential direction of the element 90, thus the lock wire is not shown. Also, the plate 93 having openings and the tube 87 are omitted.

In the main body 381 of the overtube 380, a tubular intermediate member 310 is disposed between the first region 382 and the second region 385. A female screw member 315 is attached to the proximal end portion of the element 90B at the most proximal end side in the first region 382 so as to have a threaded screw hole 315a at the proximal end side thereof.

The female screw member 315 protruding from the element 90B enters a lumen 311 disposing in the intermediate member 310 and extending in the axial direction. A feed screw 316 is engaged in the threaded screw hole of the female screw member 315. The feed screw 316 is connected to a distal end of a torque wire 317. The torque wire 317 extends to the operation portion 100 (not shown) through a torque wire lumen 391 formed in the element 90 of the second region 385.

The intermediate member 310, the female screw 315, the feed screw 316, and the torque wire 317 configure an advance/retraction mechanism 390 for advancing/retracting the first region 382 with respect to the second region 385.

In the overtube 380 configured as described above, when the torque wire 317 is rotated around the axis, the feed screw 316 rotates with respect to the female screw member 315 such that a screwing length between the female screw member 315 and the feed screw 316 changes. Accordingly, while keeping the state in which the shape of the first region 382 is fixed, for example, it is possible to advance the position of the distal end of the main body 381 shown as the upper side in FIG. 13 to the lower side in FIG. 13. When the rotation direction of the torque wire 317 is reversed, it is also possible to retract the position of the distal end of the main body 381.

According to the overtube 380, it is possible to perform the slight adjustment of the position of the distal end of the main body 381 more precisely by combining the operation of the active-bending portion (not shown) and the advancement/retraction of the position of the distal end when the shape fixation of the first region 382 is dissolved in the state in which the shape of the second region 385 is fixed.

Figure 14:
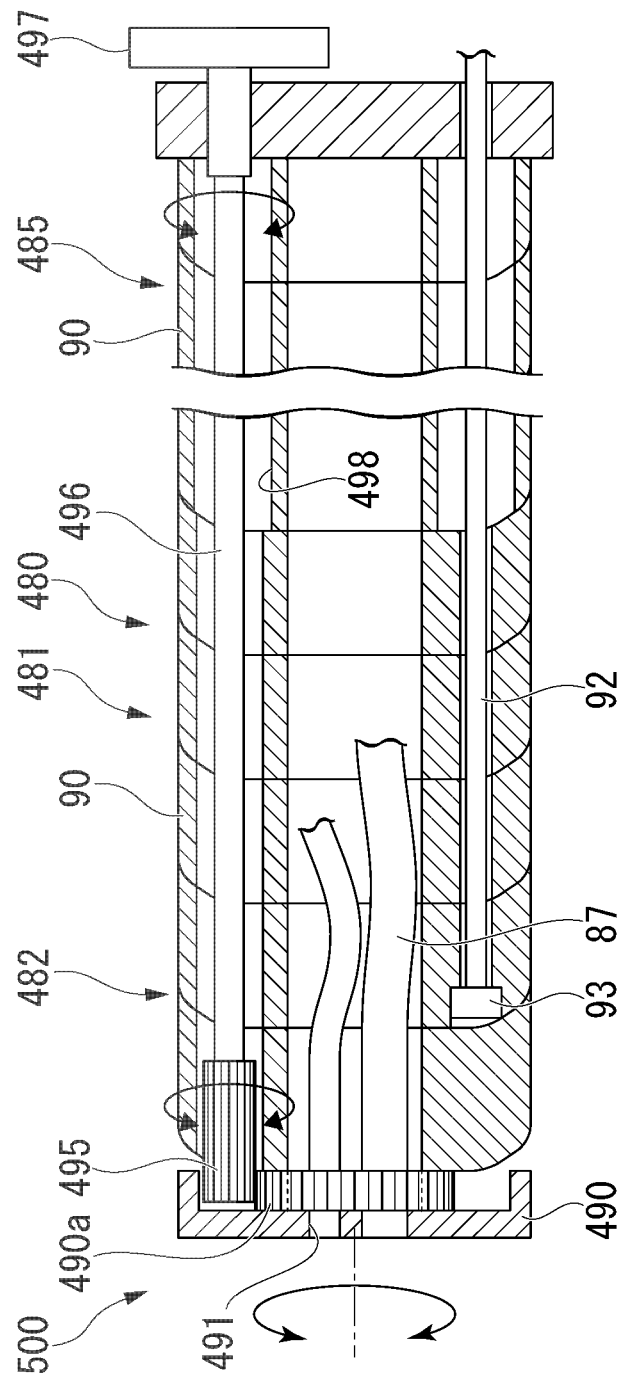
FIG. 14 is a schematic sectional view showing a medical overtube device according to another modification example of the present invention.
Figure 15:
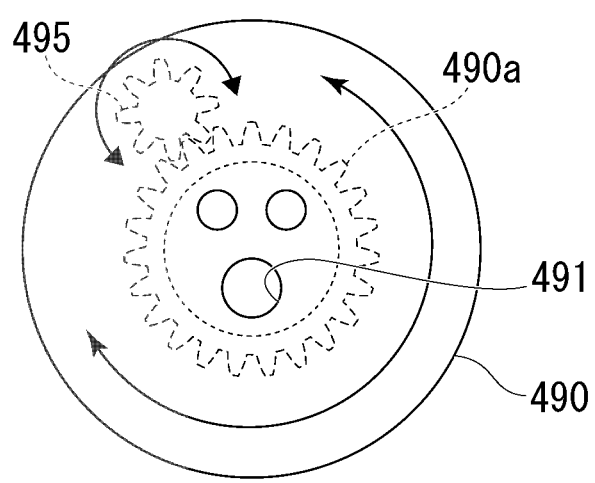
FIG. 15 is a front view showing a plate of the medical overtube device.

An overtube 480 of a modification example shown in a schematic sectional view in FIG. 14 is a configuration example of fixing the shape of the second region 485 while changing the opening position at the distal end of the first region 482.

In the overtube 480, a gear portion 490a is provided at the proximal end side of the plate 490 attached to the distal end portion of the main body 481. A plurality of openings 491 to which the tube 87 is connected are formed in a region surrounded by the gear portion 490a.

A plate operation gear 495 engaged with the gear portion 490a is disposed at the distal end of the first region 482. The plate operation gear 495 is connected to the distal end of a torque wire 496. The plate operation gear 495 and the torque wire 496 are disposed through a plate-driving lumen 498 formed in the element 90. The torque wire 496 extends to the inside of the operation portion 100 (not shown). A dial 497 for rotating the torque wire 496 is attached to the proximal portion of the torque wire 496.

The gear portion 490a, the plate operation gear 495, and the torque wire 496 configure a rotation mechanism 500 for rotating the plate 490.

In the overtube 480 having the configuration shown above, when the dial 497 is operated to rotate the torque wire 496 around the axis, the plate operation gear 495 rotates and further the gear portion 490a engaged with the plate operation gear 495 rotates. Accordingly, it is possible to adjust the positions of the openings 491 by rotating the plate 490. It is possible to rotate the plate 490 in a reversed direction by reversing the rotation direction of the torque wire 496.

According to the overtube 480, it is possible to perform the adjustment of the distal end of the main body 481 more precisely by combining the operation of the active-bending portion (not shown) and the rotation of the plate 490 when the shape fixation of the first region 482 is dissolved in the state in which the shape of the second region 485 is fixed. More specifically, not only the position of the distal end of the main body 481, but also it is possible to adjust the positional relationship between the endoscope and the treatment tool protruding from the openings 491 with respect to the target site.

The mechanisms of the overtube 380 and the overtube 480 can be individually applied or combined to be applied to the overtube disclosed in the above-described embodiments. A dial having the same configuration with the dial 497 may be attached to the torque wire 317.

Furthermore, in the above-described embodiments, the examples of fixing the shape of the main body due to the friction force between the nested-structure elements are described; however, it is possible to apply the mechanism according to the present invention to the overtube having a main body which is configured to fix the shape by negative pressure.

Furthermore, it is possible to configure either of the first region or the second region by applying the friction fixation method, and apply the negative fixation method to the other region.

Several embodiments and modification examples of the present invention have been described above, however, technical scope of the present invention is not limited to the embodiment and the application examples. Additions, omissions, substitutions and other changes in the structure are possible without departing from the spirit of the present invention.

What is claimed is:

1. A medical overtube device comprising:
    a main body formed by articulating a plurality of nested units into a first group of nested units and a second group of nested units, the main body is configured to be bendable in a longitudinal direction thereof;
    a first shape-fixation mechanism configured to fix a shape of the first group of nested units, the first shape-fixation mechanism comprises:
        a first wire, both ends of the first wire being coupled to the first group of nested units; and
        a first pulley configured to be wound by the first wire; and
    a second shape-fixation mechanism configured to fix a shape of the second group of nested units, the second shape-fixation mechanism comprises:
        a second wire, both ends of the second wire being coupled to the second group of nested units; and
        a second pulley configured to be wound by the second wire,
    wherein the first shape-fixation mechanism is configured to release the fixed shape of the first group of nested units independently from the second shape-fixation mechanism, and
    wherein the second wire comprises:
        an elongated coil sheath configured to insert the first wire therein; and
        an engagement member coupled to a distal end of the elongated coil sheath, the engagement member being configured to absorb a force from a proximal end of the first group of nested units.

2. The medical overtube device according to claim 1, further comprising:
a third pulley configured to be wound by a third wire, wherein:
one end of the third wire is coupled to a first rotation shaft of the first pulley, and
another end of the third wire is coupled to a second rotation shaft of the second pulley.

3. The medical overtube device according to claim 1, wherein the first wire is further configured to bend the first group of nested units actively.

4. A medical overtube, comprising:
a main body formed by articulating a plurality of nested units into a first group of nested units and a second group of nested units, the main body is configured to be bendable in a longitudinal direction thereof;
an advancement/retraction mechanism configured to advance and retract the first group of nested units with respect to the second group of nested units in the longitudinal direction of the main body;
a first shape-fixation mechanism configured to fix a shape of the first group of nested units, the first shape-fixation mechanism comprises:
a first wire, both ends of the first wire being coupled to the first group of nested units; and
a first pulley configured to be wound by the first wire; and
a second shape-fixation mechanism configured to fix a shape of the second group of nested units, the second shape-fixation mechanism comprises:
a second wire, both ends of the second wire being coupled to the second group of nested units; and
a second pulley configured to be wound by the second wire,
wherein the first shape-fixation mechanism is configured to release the fixed shape of the first group of nested units independently from the second shape-fixation mechanism.

5. The medical overtube device according to claim 4, further comprising:
a third pulley configured to be wound by a third wire, wherein:
one end of the third wire is coupled to a first rotation shaft of the first pulley, and
another end of the third wire is coupled to a second rotation shaft of the second pulley.

6. The medical overtube device according to claim 4, wherein the first wire is further configured to bend the first group of nested units actively.

* * * * *